United States Patent
Banavara et al.

(10) Patent No.: US 9,661,868 B2
(45) Date of Patent: May 30, 2017

(54) EXPANDED BED ADSORPTION METHODS FOR ISOLATION OF BASIC MILK PROTEINS INCLUDING LACTOFERRIN

(71) Applicant: Mead Johnson Nutrition Company, Glenview, IL (US)

(72) Inventors: Dattatreya Banavara, Newburgh, IN (US); John D. Alvey, Evansville, IN (US); Joseph Andrew Peters, Mount Vernon, IN (US); Juan M. Gonzalez, Newburgh, IN (US)

(73) Assignee: Mead Johnson Nutrition Company, Chicago, IL (US)

( * ) Notice: Subject to any disclaimer, the term of this patent is extended or adjusted under 35 U.S.C. 154(b) by 126 days.

(21) Appl. No.: 13/942,909

(22) Filed: Jul. 16, 2013

(65) Prior Publication Data

US 2015/0024462 A1   Jan. 22, 2015

(51) Int. Cl.
| | |
|---|---|
| *A23J 1/20* | (2006.01) |
| *C07K 14/79* | (2006.01) |
| *C07K 14/47* | (2006.01) |
| *C12N 9/08* | (2006.01) |

(52) U.S. Cl.
CPC .............. *A23J 1/20* (2013.01); *A23J 1/202* (2013.01); *A23J 1/205* (2013.01); *C07K 14/47* (2013.01); *C07K 14/79* (2013.01); *C12N 9/0065* (2013.01); *C12Y 111/01007* (2013.01)

(58) Field of Classification Search
CPC .. C07K 14/79; C07K 14/47; A23J 1/20; A23J 1/202; A23J 1/205; C12N 9/0065; C12Y 111/01007
See application file for complete search history.

(56) References Cited

U.S. PATENT DOCUMENTS

| | | | |
|---|---|---|---|
| 5,596,082 A * | 1/1997 | Kussendrager et al. | 530/416 |
| 5,861,491 A * | 1/1999 | Nuijens et al. | 530/417 |
| 6,096,870 A * | 8/2000 | Mozaffar et al. | 530/366 |
| 6,268,487 B1 * | 7/2001 | Kutzko et al. | 530/414 |
| 6,620,326 B1 | 9/2003 | Lihme et al. | |
| 6,977,046 B2 | 12/2005 | Hubbuch et al. | |
| 7,368,141 B2 | 5/2008 | Lihme | |
| 7,812,138 B2 | 10/2010 | Lihme et al. | |
| 2005/0065329 A1 | 3/2005 | Lihme et al. | |
| 2007/0092960 A1 * | 4/2007 | Hansen et al. | 435/239 |
| 2008/0187619 A1 * | 8/2008 | Hartmann et al. | 426/2 |
| 2014/0051831 A1 * | 2/2014 | Bertelsen et al. | 530/352 |
| 2014/0066607 A1 * | 3/2014 | Bertelsen et al. | 530/395 |

FOREIGN PATENT DOCUMENTS

| | | |
|---|---|---|
| CN | 102898516 | 1/2013 |
| EP | 0538350 | 4/1993 |
| WO | 9200799 | 1/1992 |
| WO | 9313676 | 7/1993 |
| WO | 9717132 | 5/1997 |
| WO | 9808603 | 3/1998 |
| WO | 0218237 | 3/2002 |
| WO | 0373866 | 9/2003 |
| WO | 2004082397 | 9/2004 |
| WO | 2006132553 | 12/2006 |

OTHER PUBLICATIONS

Makino et al. High-performance liquid chromatographic separation of human apolactoferrin and monoferric and diferric lactoferrinsv' (Journal of Chromatography 1992 579 346-349).*
Qiao-Yan, D. et al., "One-Step Purification of Lactoferrin from Crude Sweet Whey Using Cation-Exchange Expanded Bed Absorption," Ind. Eng. Chem. Res. 2013, 52, 2693-2699.
Clark, N., "High-Value proteins from crude whey in a Rhobust® manner," Nutrafoods 2009, 8(4).

* cited by examiner

*Primary Examiner* — Alexander Kim
(74) *Attorney, Agent, or Firm* — OspreyIP, PLLC; James R. Cartiglia; Bethany J. Whelan

(57) ABSTRACT

The present disclosure relates to improved expanded bed adsorption processes for isolating proteins from milk sources. In particular embodiments, the present disclosure provides a process for isolating a milk protein, such as lactoferrin, from a milk source comprising establishing an expanded bed adsorption column comprising a particulate matrix, applying a milk source to the matrix, and eluting the lactoferrin from the matrix with an elution buffer comprising about 0.3 to about 2.0 M sodium chloride.

15 Claims, No Drawings

EXPANDED BED ADSORPTION METHODS FOR ISOLATION OF BASIC MILK PROTEINS INCLUDING LACTOFERRIN

TECHNICAL FIELD

The present disclosure relates to improved processes for the isolation of basic milk proteins (e.g., proteins that have an isoelectric point (pI) value higher than 7.0) or peptides, such as lactoferrin, using expanded bed adsorption chromatography.

BACKGROUND

Nutritional compositions for infants generally seek to mimic the composition and function of human breast milk. Lactoferrin is an 80-kDa member of the transferrin family of iron-binding glycoproteins, and is one of the primary proteins in human milk. Lactoferrin has the capacity to reversibly bind two iron cations, even at low pH, and can facilitate iron uptake in the human intestine. Functionally, lactoferrin regulates iron absorption and can bind iron based free radicals as well as donate iron for an immunological response. Additionally, lactoferrin exhibits antibacterial activity. Thus, it would useful to include lactoferrin in commercial infant formulas.

However, the use of lactoferrin in infant formulas has been limited by the lack of large-scale, commercially useful sources. Bovine lactoferrin, which has about 69% sequence homology to human lactoferrin, can be obtained from cow's milk by a variety of purification methods, but such processes are inefficient for widespread commercial use. Other non-human lactoferrins include porcine lactoferrin, equine lactoferrin, buffalo lactoferrin, goat lactoferrin, murine lactoferrin, and camel lactoferrin, but similar production inefficiencies exist.

The concentration of lactoferrin in bovine whey, for example, is generally only about 10 to 100 mg/liter. Stabilized fluid bed adsorption, also called Expanded Bed Adsorption (EBA) is one process for obtaining proteins from a raw material, such as bovine lactoferrin from cow's milk sources. EBA enables the isolation of biomolecules, such as proteins and plasmids, directly from a crude feed stock using a particulate chromatographic matrix, in which the matrix remains fluidized during loading of the feed stock and optionally during elution. Because the matrix is fluidized during loading, solids and undesired materials pass through the matrix, which avoids fouling of the chromatographic material. Thus, EBA can, in certain circumstances, combine the effects of centrifugation, filtration, concentration and purification into a single process, thereby saving time and minimizing pre-processing purifying steps. However, current EBA technology has several disadvantages in isolating lactoferrin from milk sources. In particular, current EBA technology still uses a relatively large volume of liquid and also uses a high concentration of sodium hydroxide (e.g. 200 mM) during elution of the lactoferrin, which may cause irreversible structural changes due to denaturing of the protein.

Additionally, non-human mammalian milk sources contain other useful proteins, including lactoperoxidase, α-lactalbumin, β-lactoglobulin, immunoglobulins, glycopeptides, glycomacropeptide, whey protein isolates, and lysozyme. These proteins and mixtures also may useful as food ingredients or nutritional supplements. Thus, there is a need for improved processes for isolating and purifying lactoferrin and other proteins from milk sources on a commercial scale for use in nutritional products, such as infant formulas.

BRIEF SUMMARY

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

The present disclosure provides improved EBA processes for isolating proteins from milk sources. In particular embodiments, the present disclosure provides a process for isolating a milk protein, such as lactoferrin, from a milk source comprising establishing an expanded bed adsorption column comprising a particulate matrix, applying a milk source to the matrix, and eluting the lactoferrin from the matrix with an elution buffer comprising about 0.3 to about 2.0 M sodium chloride. Any mammalian milk source may be used in the present processes, although in particular embodiments, the milk source is a bovine milk source. The milk source comprises, in some embodiments, whole milk, reduced fat milk, skim milk, whey, casein, or mixtures thereof.

DETAILED DESCRIPTION

Reference now will be made in detail to the embodiments of the present disclosure, one or more examples of which are set forth herein below. Each example is provided by way of explanation of the nutritional composition of the present disclosure and is not a limitation. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present disclosure, including components thereof, can comprise, consist of, or consist essentially of the essential elements and limitations of the embodiments described herein, as well as any additional or optional steps.

As used herein, the term "about" should be construed to refer to both of the numbers specified in any range. Any reference to a range should be considered as providing support for any subset within that range.

The present disclosure relates to improved processes for purifying proteins from a raw material, such as a mammalian milk source, using EBA. The milk source can be, in certain embodiments, whole milk, skim milk, reduced fat milk, or a product derived from milk, such as whey or casein. While the milk source can be any mammalian milk source, in particular embodiments, it is a bovine milk source, and more particularly, bovine whey. In particular embodiments, the target protein is lactoferrin, though other milk proteins, such as lactoperoxidases or lactalbumins, also may be isolated. EBA is particularly suitable for handling large volumes of crude feed material and is therefore useful for producing commercially useful amounts of purified milk proteins. In some embodiments, the process comprises the steps of establishing an expanded bed adsorption column comprising a particulate matrix, applying a milk source to the matrix, and eluting the lactoferrin from the matrix with about 0.3 to about 2.0 M sodium chloride. In other embodiments, the lactoferrin is eluted with about 0.5 to about 1.0 M sodium chloride, while in further embodiments, the lactoferrin is eluted with about 0.7 to about 0.9 M sodium chloride.

The expanded bed adsorption column can be any known in the art, such as those described in U.S. Pat. Nos. 7,812,138, 6,620,326, and 6,977,046. In some embodiments, the column is be equipped with at least one inlet and at least one outlet, and can be operated in both an expanded mode and a packed mode. More particularly, in certain embodiments, a milk source is applied to the column in an expanded mode, and the elution is performed in either expanded or packed mode. In particular embodiments, the elution is performed in an expanded mode. For example, the expansion ratio in the expanded mode may be about 1 to about 3, or about 1.3 to about 1.7. EBA technology is further described in international published application nos. WO 92/00799, WO 02/18237, WO 97/17132, which are hereby incorporated by reference in their entireties.

The EBA column comprises an adsorbent particulate matrix material comprising small particles with a large density, thereby allowing a high flow rate in an expanded mode. The adsorbent particulate matrix material may be any matrix suitable for EBA. The density and size of the particles influence the flow rate and expansion ratio of the system. For example, in some embodiments, the particle density is 1.3 g/mL or more, for example, at least 1.5 g/mL, at least 1.8 g/mL, at least 2.0 g/mL, or at least 2.3 g/mL. In particular embodiments, the particle size is in a range of about 1.5 to about 3.5 mg/mL, or about 2.5 to 3.5 mg/mL. The density of the adsorbent particles as used herein refers to density of the particles in a fully solvated state, as opposed to the density of dried adsorbant particles.

Furthermore, in some embodiments, the particle size distribution of the matrix ranges from about 10 μm to about 1000 μm. For example, in certain embodiments, the particle size distribution ranges from about 25 μm to about 1000 μm, or about 50 μm to about 800 μm, or about 80 μm to about 600 μm in size. In other embodiments, the particle size of the matrix is less than about 300 μm, less than about 150 μm, or less than about 120 μm. in particular embodiments, the particle sizes range from about 40 to about 150 μm, about 40 to about 120 μm, about 40 to about 100 μm, or about 40 to about 70 μm.

The isoelectric point of lactoferrin is approximately 8.9. Prior EBA methods of isolating lactoferrin use 200 mM sodium hydroxide as an elution buffer. Thus, the pH of the system rises to over 12, and the structure and bioactivity of lactoferrin may be comprised, by irreversible structural changes. It has now been discovered that a sodium chloride solution can be used as an elution buffer in the isolation of lactoferrin from the EBA matrix. In certain embodiments, the sodium chloride has a concentration of about 0.3 M to about 2.0 M. In other embodiments, the lactoferrin elution buffer has a sodium chloride concentration of about 0.3 M to about 1.5 M, or about 0.5 m to about 1.0 M.

In certain embodiments, the lactoferrin elution buffer may be recirculated one or more times, thereby reducing the total elution volume. For example, the elution buffer may be recirculated 2, 3 or more times. In some embodiments, the elution buffer may be recirculated from about 1 to about 10 times, or about 1 to about 5 times. An elevated elution buffer temperature also may, in certain embodiments, improve the efficiency of the elution of lactoferrin. The temperature of the sodium chloride elution buffer may be, in certain embodiments, about 30 to about 50° C.

In certain embodiments, the milk source comprises lactoperoxidase. Lactoperoxidase binds to the EBA matrix with lower affinity than lactoferrin, and therefore, may be eluted with a sodium chloride solution having a concentration of about 0.2 to about 0.3 M prior to eluting the lactoferrin. In some embodiments, the lactoperoxidase elution buffer is recirculated several times in order to reduce carryover of lactoperoxidase into the lactoferrin fraction. For example, the buffer may be recirculated 1, 2, 3 or more times, or about 1-10 times or about 1-5 times. Furthermore, lactoperoxidase may be isolated from the buffer if desired. In other embodiments, an intermediate flush of lactoperoxidase may be performed during the step of applying the milk source to the EBA column (feed stock loading). Flushing some or all of the lactoperoxidase during column loading is believed to improve the binding of lactoferrin to the matrix, thereby improving the yield of lactoferrin.

In certain embodiments, the milk source is subjected to a diafiltration procedure prior to loading it on the EBA column. For example, in embodiments using dairy whey as the milk source, the ionic strength of the whey may hinder adsorption of basic proteins, such as lactoferrin, onto the EBA matrix. Diafiltration is a form of membrane filtration used in industry for purifying and concentrating macromolecular solutions, such as protein-containing solutions. During diafiltration hydrostatic pressure forces a liquid against a semipermeable membrane. Water is continuously added to the feed stream to maintain the same volume of the feed. Suspended solids and solutes of high molecular weight are retained, while low molecular weight solutes pass through the membrane. Without being bound by any particular theory, it is believed that diafiltration of the milk source, such as whey, will increase adsorption of proteins to the EBA matrix. Furthermore, diafiltration may also remove or reduce lactose and mineral ions that can interfere with adsorption of basic proteins to EBA matrix. Therefore, diafiltration may also reduce the total volume of liquid used throughout the process if desired. Accordingly, in certain embodiments, the milk source comprises diafiltered whey, and more particularly, diafiltered bovine whey.

Basic proteins in whey and milk are a minor fraction of the total protein content. It is possible that molecular interactions of these proteins may also hinder adsorption to the EBA matrix. While not being bound by any particular theory, it is believed that citrates may disrupt the water structure around the proteins and prevent these molecular interactions. Accordingly, in some embodiments, citrates are added to the milk source prior to applying the milk source to the EBA column. Citrates that can be added to the milk source include sodium citrate, potassium citrate, magnesium citrate, and the like. The concentration of citrate salts can range from about 0.01% to about 2% w/v of the milk source, while in other embodiments, the concentration of citrate salt can range from about 0.2% to about 0.8% w/v of the milk source. For example, when the milk source is whey, the concentration can be, in some embodiments, about 0.02% to about 0.8% w/v (assuming 0.8% protein and 9% solids for whey). In some embodiments, on a protein basis, the citrate salt quantity can range from about 0.025:1 to about 1:1, while in other embodiments, the ratio can be about 0.05:1 to about 0.1:1.

In other embodiments, the method further comprises adding iron salts to the milk source, such as whey. Alternatively, feed pH can be changed to release the bound iron from lactoferrin. Again, not being bound by theory, varying the percent iron saturation of the lactoferrin may further improve binding of lactoferrin to the matrix, thereby improving total recovery of lactoferrin from the milk source. Any water soluble iron salt is suitable for this purpose, including ferrous sulfate and ferric chloride. The concentration of the iron salt is dependent on the level of lactoferrin in the feed. The ratio of lactoferrin to the iron source can range from about 200-1000 mg of iron per kg of lactoferrin.

In other embodiments, the temperature of the raw milk source may have an impact on the adsorption to the EBA matrix. Accordingly, in certain embodiments, the milk source is at a temperature of less than 40° F., for example between about 32 and 40° F., or between about 35 and 40° F.

The flow rate during elution of lactoferrin can be about 100 to about 200 L/hr. In some embodiments, the flow rate is about 125 to about 175 L/hr, or about 130 to about 160 L/hr.

Useful matrix materials in the EBA system include those described in EP 0538 350, and U.S. Pat. Nos. 6,620,326, 6,977,046, 7,812,138, and 7,368,141, which are herein incorporated by reference in their entirety. In general, the matrix comprises particles that can adsorb the desired protein. In certain embodiments, the matrix comprises particles having a non-porous, high density core coated with a porous adsorbent material. The density and diameter of the matrix particles determine the flow rate to which the particles may be exposed without being flushed out of the column. In certain embodiments, the density of the particles is at least 1.5 g/mL, particularly about 2.5 to about 3.5 g/mL (wet) and the average particle size ranges from about 80 to about 600 μm.

In some embodiments, the particle matrix is at least partly permeable to the protein to be isolated in order to provide sufficient binding capacity. The particles in the matrix may be any structure composition and shape. In particular embodiments, the particles comprise a non-porous core material coated with an adsorbent base material. The non-porous core has a higher density than the particle as a whole. For example, the non-porous core may, in certain embodiments, have a density of at least 4.0 g/ml. More particularly, the matrix may comprise a conglomerate type material or a pellicular type material. A conglomerate material comprises at least two non-porous cores surrounded by the adsorbent base material. For example, a conglomerate matrix comprises in some embodiments different types and sizes of non-porous materials held together by the adsorbent base material, such as two or more high density particles held together by agarose. A pellicular type material comprises, in some embodiments, particles, wherein each particle contains a single high density core material coated with a layer of the adsorbent base material. For example, the pellicular material in some embodiments comprises a glass bead coated with agarose or a stainless steel particle coated with agarose.

The particle, as stated, comprises a high density non-porous core with a porous material surrounding the core. In certain embodiments, the adsorbent base material further comprises a ligand. In certain embodiments, the non-porous core constitutes typically of at most 50% of the total volume of the adsorbent particle, such as at most 40%, preferably at most 30%. Examples of suitable non-porous core materials are inorganic compounds, metals, heavy metals, elementary non-metals, metal oxides, non-metal oxides, metal salts and metal alloys, etc. as long as the density criteria above are fulfilled. Examples of such core materials are metal silicates metal borosilicates; ceramics including titanium diboride, titanium carbide, zirconium diboride, zirconium carbide, tungsten carbide, silicon carbide, aluminum nitride, silicon nitride, titanium nitride, yttrium oxide, silicon metal powder, and molybdenum disilide; metal oxides and sulfides, including magnesium, aluminum, titanium, vanadium, chromium, zirconium, hafnium, manganese, iron, cobalt, nickel, copper and silver oxide; non-metal oxides; metal salts, including barium sulfate; metallic elements, including tungsten, zirconium, titanium, hafnium, vanadium, chromium, manganese, iron, cobalt, nickel, indium, copper, silver, gold, palladium, platinum, ruthenium, osmium, rhodium and iridium, and alloys of metallic elements, such as alloys formed between said metallic elements, e.g. stainless steel; crystalline and amorphous forms of carbon, including graphite, carbon black and charcoal. Preferred non-porous core materials are tungsten carbide, tungsten, steel and titanium beads, such as stainless steel beads.

The porous base material, in certain embodiments, is a polymeric base matrix used to cover and keep multiple (or a single) core materials together and to bind an adsorbing ligand. The polymeric base matrix comprises, in come embodiments, natural or synthetic organic polymers, typically selected from i) natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses; ii) synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionally, and substituted derivatives thereof; and iii) mixture thereof. In particular embodiments, the polymeric base material is a polysaccharide, such as agarose.

In certain embodiments, the matrix material is able to bind a high amount of the desired protein per volume unit of the adsorbent. For example, in certain embodiments, at least 50% of the particle volume comprises the adsorbent base material, preferably at least 70%, more preferably at least 80% and most preferably at least 90% of the volume of the adsorbent particles. In particular embodiments, the adsorbent base material includes at least one ligand.

Particle size analysis can be performed using a computerized image analysis of the bead population giving the number of particles at any given particle diameter in relation to the total number of particles analyzed in the specific measurement. Typically the total number of particles analyzed will be in the range of 250-500 particles). These particle size data may be transferred into the volume percent represented by each particle size by a routine mathematical transformation of the data, calculating the volume of each bead and relating this to the total volume occupied by all beads counted in the measurement.

The particle size distribution according to the disclosure is preferably defined so that more than 90% of the particles are found between 20-500% of the mean particle diameter, more preferable between 50-200% of the mean particle diameter, most preferable between 50-150% of the mean particle diameter.

The preferred shape of a single adsorbent particle is substantially spherical. The overall shape of the particles is, however, normally not critical, thus, the particles can have other types of rounded shapes, e.g. ellipsoid, droplet and bean forms. However, for certain applications (e.g. when the particles are used in a fluidized bed set-up), it is preferred that at least 95% of the particles are substantially spherical.

Some embodiments, the matrix comprises agarose-coated tungsten-carbide beads. A commercially available source of agarose coated tungsten-carbide beads is FastLine® SP from Upfront Chromatography A/S.

Preparation of the particulate material useful in the methods described herein may be performed by various methods known per se (e.g. by conventional processes known for the person skilled in the art, see e.g. EP 0 538 350 B1 or WO 97/17132). For example, by block polymerization of monomers; suspension polymerization of monomers; block or suspension gelation of gel-forming materials, e.g. by heating and cooling (e.g. of agarose) or by addition of gelation "catalysts" (e.g. adding a suitable metal ion to alginates or carrageenans); block or suspension cross-linking of suitable soluble materials (e.g. cross linking of dextrans, celluloses, or starches or gelatins, or other organic polymers with e.g. epichlorohydrin or divinyl sulphone); formation of silica polymers by acidification of silica solutions (e.g. block or suspension solutions); mixed procedures e.g. polymerization and gelation; spraying procedures; and fluid bed coating of density controlling particles; cooling emulsions of density controlling particles suspended in polymeric base matrices in heated oil solvents; or by suspending density controlling particles and active substance in a suitable monomer or copolymer solution followed by polymerization.

In some embodiments, a particulate material comprising agarose as the polymeric base matrix and steel beads as the core material is obtained by heating a mixture of agarose in water (to about 95° C.), adding the steel beads to the mixture and transferring the mixture to a hot oil (e.g. vegetable oils), emulsifying the mixture by vigorous stirring (optionally by adding a conventional emulsifier) and cooling the mixture. It will be appreciated by the person skilled in the art that the particle size (i.e. the amount of polymeric base matrix (here: agarose) which is incorporated in each particle can be adjusted by varying the speed of the mixer and the cooling process. Typically, following the primary production of a particle preparation the particle size distribution may be further defined by sieving and/or fluid bed elutriation.

The porous matrix, such as polymer agarose, is in certain embodiments, chemically derivatized with a low molecular weight compound referred to herein as the ligand such that the adsorbent comprises a ligand with affinity to proteins. The ligand constitutes the adsorbing functionality of the adsorbent media or the polymeric backbone of the adsorbent particle has a binding functionality incorporated per se. Well-known ligand chemistries such as cation exchangers, e.g. sulphonic acid, have been proven to be efficient tools for purification of whey proteins such as lactoferrin and lactoperoxidase. These proteins are positively charged, even at neutral pH, and selective interaction with a cation exchanger can be obtained. Other proteins require more sophisticated binding interaction with the ligand in order to obtain a selective adsorption.

Such affinity ligands, like the chargeable moieties, may be linked to the base matrix by methods known to the person skilled in the art, e.g. as described in "Immobilized Affinity Ligand Techniques" by Hermanson et al., Academic Press, Inc., San Diego, 1992. In cases where the polymeric base matrix does not have the properties to function as an active substance, the polymeric base matrix (or matrices where a mixture of polymers are used) may be derivatized to function as an active substance in the procedures of activation or derivatization. Thus, materials comprising hydroxyl, amino, amide, carboxyl or thiol groups may be activated or derivatized using various activating chemicals, e.g. chemicals such as cyanogen bromide, divinyl sulfone, epichlorohydrin, bisepoxyranes, dibromopropanol, glutaric dialdehyde, carbodiimides, anhydrides, hydrazines, periodates, benzoquinones, triazines, tosylates, tresylates, and diazonium ions. Examples of methods for chemical derivatization and specific ligands useful in certain embodiments are described in WO 98/08603.

The ligand concentration can impact the adsorption strength in certain embodiments. For example, in an embodiment, the adsorbent carries ligands for adsorption of the desired protein in a concentration of at least 20 nM, such as at least 30 mM or at least 40 mM, preferably at least 50 mM and most preferably at least 60 mM.

A subset of adsorbents may be characterized in terms of their binding capacity to bovine serum albumin (BSA). This subset of adsorbents are typically those comprising a ligand selected from the group consisting of i) ligands comprising aromatic or heteroaromatic groups (radicals) of the following types as functional groups: benzoic acids such as 2-aminobenzoic acids, 3-aminobenzoic acids, 4-aminobenzoic acids, 2-mercaptobenzoic acids, 4-amino-2-chlorobenzoic acid, 2-amino-5-chlorobenzoic acid, 2-amino-4-chlorobenzoic acid, 4-aminosalicylic acids, 5-aminosalicylic acids, 3,4-diaminobenzoic acids, 3,5-diaminobenzoic acid, 5-aminoisophthalic acid, 4-aminophthalic acid; cinnamic acids such as hydroxy-cinnamic acids; nicotinic acids such as 2-mercaptonicotinic acids; naphthoic acids such as 2-hydroxy-1-naphthoic acid; quinolines such as 2-mercaptoquinoline; tetrazolacetic acids such as 5-mercapto-1-tetrazolacetic acid; thiadiazols such as 2-mercapto-5-methyl-1,3,4-thiadiazol; benzimidazols such as 2-amino-benzimidazol, 2-mercaptobenzimidazol, and 2-mercapto-5-nitrobenzimidazol; benzothiazols such as 2-aminobenzothiazol, 2-amino-6-nitrobenzothiazol, 2-mercaptobenzothiazol and 2-mercapto-6-ethoxybenzothiazol; benzoxazols such as 2-mercaptobenzoxazol; thiophenols such as thiophenol and 2-aminothiophenol; 2-(4-aminophenylthio)acetic acid; aromatic or heteroaromatic sulfonic acids and phosphonic acids, such as 1-amino-2-naphthol-4-sulfonic acid and phenols such as 2-amino-4-nitro-phenol.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

EXAMPLE

Production of Lactoperoxidase and Lactoferrin

Lactoperoxidase and lactoferrin were separated from bovine whey using an EBA method. FastLine® SP agarose coated tungsten-carbide adsorbent was used, with a settled bed height of 40 cm, and a total volume of 3140 mL. Whey was loaded on the column with a flow rate of about 240 L/hr. The flow rate during rinse and elution was about 148-158 L/hr. Lactoperoxidase was eluted with 250 mM NaCl, and lactoferrin was eluted with 0.8 M NaCl. Recirculation of the eluent reduced the total volume of eluent from 55 L to 39 L used without losing the total amount of lactoferrin recovered from the whey.

Lactoferrin and Lactoperoxidase concentration ere determined by reverse-phase high-pressure liquid chromatography (HPLC) on a polystyrene-divinyl benzene column. Purified lactoferrin was obtained from Upfront Chromatography A/S and used as a standard. Bovine lactoperoxidase standard was obtained from Worthington Biochemical Corp. Sample were received in aqueous solutions, spiked with lactoferrin and lactoperoxidase standard solutions to prepare a two-point standard addition curve, filtered and collected in silanized vials for injection into the HPLC system. The proteins were eluted with acetonitrile using a 20-90% linear gradient and detected at 214 nm.

The total recovery of lactoferrin was 63%. Overall, the NaCl process yields about 40 g of lactoferrin per 1000L, while the NaOH process yields 27 g of lactoferrin per 1000 L.

What is claimed is:

1. A process for isolating lactoferrin from a milk from a non-human source, wherein the process comprise the following steps performed in the following order:
   (1) establishing an expanded bed adsorption column comprising a particulate matrix,
   (2) subjecting the milk from the non-human source to a diafiltration procedure prior to applying to the expanded bed column to remove low molecular weight solutes from the milk from the non-human source to produce a filtered milk source;
   (3) adding citrates to the filtered milk source, wherein the amount of citrate is from about 0.01% to about 2.0% w/v of the filtered milk source;
   (4) applying the filtered milk source including citrates to the matrix of the expanded bed column,
   (5) eluting the lactoperoxidase from the matrix with a first elution buffer consisting essentially of 250 mM NaCl, and
   (6) eluting the lactoferrin from the matrix with a second elution buffer comprising about 0.3 to about 2.0 M sodium chloride, wherein the elution buffer has a temperature of about 30° C. to about 50° C.

2. The process of claim 1, further comprising recirculating the second elution buffer at least once.

3. The process of claim 1, wherein the eluting step of (5) and (6) is performed in a fluidized mode.

4. The process of claim 3, wherein the eluting step of (5) and (6) is performed at a flow rate of about 100 to about 200 L/hr.

5. The process of claim 3, wherein the matrix has an expansion ratio of at least 1 during the elution.

6. The process of claim 1, wherein the eluting step of (5) and (6) is performed in an expanded mode.

7. The process of claim 1, further comprising the step of adding an iron salt to the filtered milk source prior to subjecting the filtered milk source to the matrix.

8. The process of claim 7, wherein the iron salts are added in an amount of from about 200 mg to about 1000 mg of iron per kg of lactoferrin present in the filtered milk source.

9. The process of claim 1, wherein the matrix comprises cross-linked agarose and tungsten carbide.

10. The process of claim 1, wherein the matrix has a density of about 2.5 to about 3.5 mg/mL.

11. The process of claim 1, wherein the milk from the non-human source is a bovine milk source.

12. The process of claim 11, wherein the milk the non-human source is whole milk, skim milk, reduced fat milk, whey, casein, or a combination thereof.

13. The process of claim 12, wherein the milk the non-human source is bovine whey.

14. The process of claim 1, wherein the milk the non-human source is ultrafiltered bovine whey.

15. The process of claim 1, wherein the second elution buffer does not include sodium hydroxide.

* * * * *